US00PP30298P2

(12) United States Plant Patent
Greppi

(10) Patent No.: US PP30,298 P2
(45) Date of Patent: Mar. 19, 2019

(54) ***MECARDONIA* PLANT NAMED 'INTAMEC003'**

(50) Latin Name: *Mecardonia procumbens*
Varietal Denomination: INTAMEC003

(71) Applicant: Instituto Nacional de Technologia Agropecuaria, Ciudad Autonoma de Buenos Aires (AR)

(72) Inventor: Julian A. Greppi, Ciudad Autonoma de Buenos Aires (AR)

(73) Assignee: Instituto Nacional de Tecnologia Agropecuaria, Ciudad Autonoma de Buenos Aires (AR)

( * ) Notice: Subject to any disclaimer, the term of this patent is extended or adjusted under 35 U.S.C. 154(b) by 0 days.

(21) Appl. No.: 15/732,153

(22) Filed: Sep. 26, 2017

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/02; A01H 5/00; A01H 6/68
See application file for complete search history.

(56) References Cited

PUBLICATIONS

Sosa et al. Chromosome numbers and DNA content in some species of *Mecardonia* (Gratiolae, Plantaginaceae), CompCytogen 10(4):769-780 (2016). (Year: 2016).*

* cited by examiner

*Primary Examiner* — June Hwu
(74) *Attorney, Agent, or Firm* — Barbara Campbell; Cochran Freund & Young LLC

(57) ABSTRACT

A *Mecardonia* plant particularly distinguished by having yellow flower color, a very compact plant growth habit, and large leaves, is disclosed.

1 Drawing Sheet

Genus and species: *Mecardonia procumbens.*
Variety denomination: 'INTAMEC003'.

BACKGROUND OF THE NEW PLANT

The present invention relates to a new and distinct variety of *Mecardonia* plant, botanically known as *Mecardonia procumbens*, and hereinafter referred to by the variety name 'INTAMEC003'.

'INTAMEC003' originated from a hybridization made in 2009 in Buenos Aires, Argentina. The female parent was a wild access of *Mecardonia procumbens* var. *flagellaris*, characterized by its large yellow flowers, early flowering, medium internodes, large leaves and upright plant growth habit. The male parent was a proprietary, unpatented *Mecardonia procumbens* var. *tenella* line named 'AM5-264', characterized by its abundant yellow flower color, short internodes, sort leaves and compact creeping plant growth habit.

In March 2010, both parental lines were crossed and seeds were obtained. The seeds were harvested after 30 days. The progeny was multiplied by cuttings during June 2011. In winter 2011, twenty genotypes which were evaluated and selected for characteristics of early flowering and compact plant growth habit. These selected plants were evaluated in field trials and pots. In January 2012, twelve of the twenty genotypes were selected for evaluation in Japan. From the evaluations done in Argentina and Japan the cultivar line 'G2012-28' was produced meeting the desired characteristics of very early vigorous blooms, large flowers and very compact habit. 'G2012-28' is also sterile.

In January 2013, rooted cuttings were produced. In August 2013, the breeder confirmed that 'G-2012-28' fixed and stable. 'G2012-28' was propagated and cultivated again at the Chogo research station in Chogo, Fujisawa, Kanagawa Prefecture, Japan to reconfirm the lines' stability. The line was subsequently named 'INTAMEC003' and its unique characteristics were found to reproduce true to type in successive generations of asexual propagation.

SUMMARY

The following are the most outstanding and distinguishing characteristics of this new variety when grown under normal horticultural practices in Salinas, Calif.

1. Yellow flower color;
2. A very compact plant growth habit; and
3. Large leaves.

DESCRIPTION OF THE PHOTOGRAPHS

This *Mecardonia* plant is illustrated by the accompanying photographs which show the plant's overall plant habit including form, foliage, and flowers. The photographs are of a four-month-old plant grown from stick date in Salinas, Calif. under greenhouse conditions in 2017. The colors shown are as true as can be reasonably obtained by conventional photographic procedures.

DESCRIPTION OF THE NEW VARIETY

Figure 1:
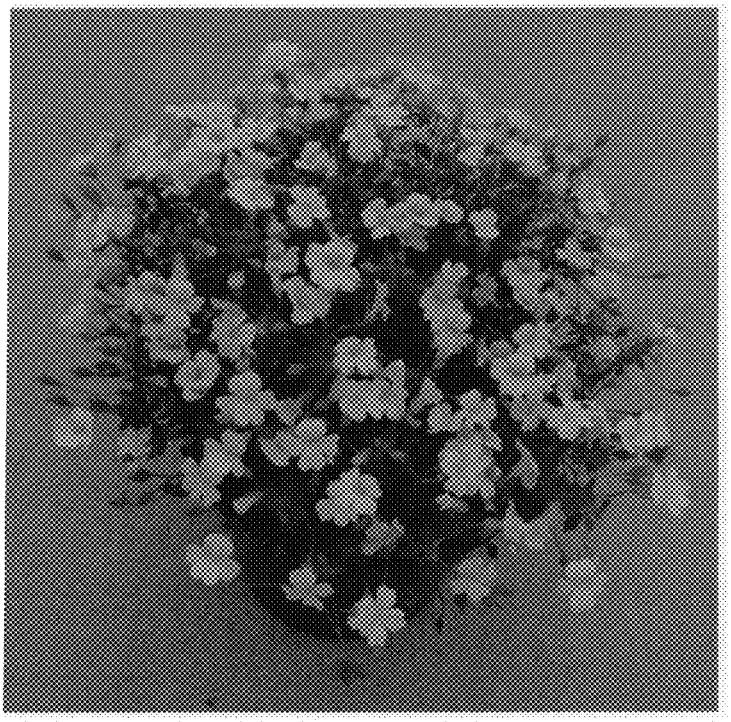
FIG. 1 shows the overall plant habit of the plant grown in a pot.
Figure 2:
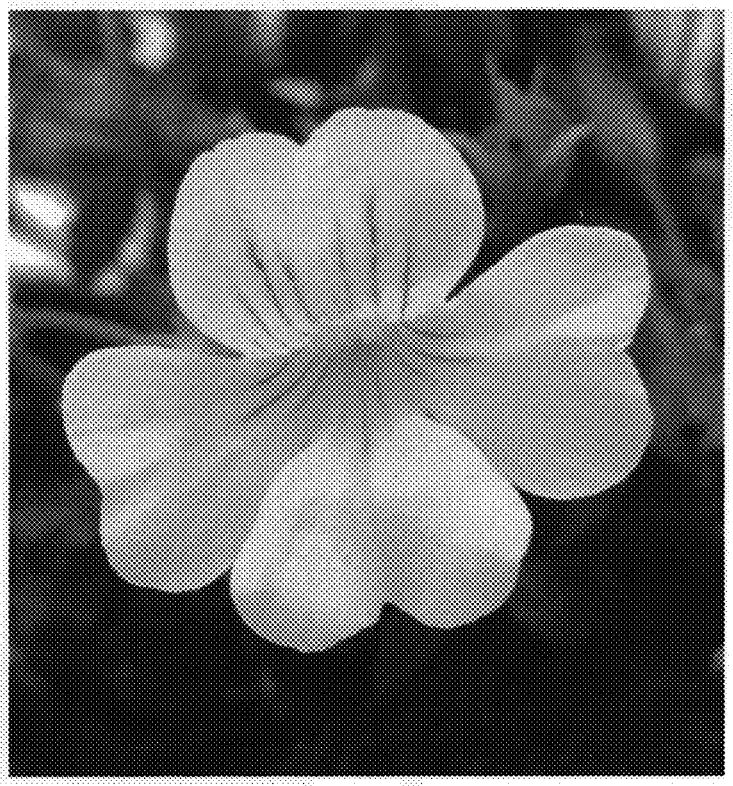
FIG. 2 shows a close-up of the mature inflorescence of the plant.

The following detailed descriptions set forth the distinctive characteristics of 'INTAMEC003'. The data which define these characteristics were collected from asexual reproductions carried out in Salinas, Calif. Data was collected on four-month-old plants from stick date grown under greenhouse conditions in Salinas, Calif. in 2017. Color references are to The R.H.S. Colour Chart of The Royal Horticultural Society of London (R.H.S.), 4th edition (2001).

Classification:

*Family*.—Plantaginaceae.

*Botanical*.—*Mecardonia procumbens*.

*Common*.—*Mecardonia*, axilflower.

*Designation*.—'INTAMEC003'.

Parentage:

*Female parent*.—A wild access of *Mecardonia procumbens* var. *flagellaris* (unpatented).

*Male parent*.—Proprietary *Mecardonia* line 'AM5-264' (unpatented).

Growth:

*Time to produce a rooted cutting*.—About 6 weeks. The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit*.—Compact.

*Height*.—10.0 cm from soil line to top of foliage.

*Spread*.—22.0 cm.

*Life cycle*.—Tender perennial.

*Form*.—Domed, moderately dense.

*Time to bloom from propagation*.—10 weeks.

*Flowering requirements*.—Will flower so long as day length is greater than 12 hours and temperature exceeds 13° C.

*Resistance/susceptibility*.—None observed. Not known to have resistance to pathogens and pests common to *Mecardonia* plants.

Branches:

*Branch color*.—RHS 146B (Yellow-Green).

*Anthocyanin color*.—Absent.

*Surface texture*.—Glabrous; pubescence absent.

*Branch description*.—Dull, circular cross-section.

*Branch strength*.—Moderate.

*Branch diameter*.—1.0 mm.

*Branch length*.—8.0 cm.

*Internode length*.—7.0 mm to 9.0 mm.

Leaves:

*Arrangement*.—Opposite, simple.

*Shape*.—Elliptic.

*Tip*.—Acute.

*Base*.—Attenuate.

*Margin*.—Serrate.

*Attachment*.—Decurrent.

*Surface texture*.—Smooth, glabrous (upper and lower).

*Length*.—1.1 cm.

*Width*.—0.4 cm.

*Color*.—Upper surface: RHS 147A (Yellow-Green). Lower surface: RHS 136B (Yellow-Green).

*Fragrance*.—Absent.

*Surface pubescence*.—Absent.

*Petiole*.—Length: 1.5 mm. Diameter: 1.0 mm. Color: Closest to RHS 147B (Yellow-Green) (upper and lower surface). Texture: Smooth, glabrous.

*Venation pattern*.—Pinnate.

*Venation color*.—Closest to RHS 146C (Yellow-Green) (upper and lower).

Flowers:

*Inflorescence type*.—Solitary axillary flowers that face mostly upward to outwardly; freely flowering with approximately 250 to 300 flowers open at a given time; composed of 4 fused petals.

*Blooming season*.—Spring to Fall.

*Flower diameter*.—1.6 cm.

*Flower depth*.—0.9 cm.

*Flowering habit*.—Indeterminate.

*Duration of flower life*.—5 days.

*Flower corolla arrangement*.—Bilabiate corolla with one upper petal lobe, three lower petal lobes, and a corolla tube.

*Fragrance*.—Absent.

*Flower shape*.—Ovate.

*Corolla lobe arrangement*.—Mostly open, but some touching and slightly overlapping.

*Petal lobes*.—Texture: Smooth, glabrous, upper petal lobe with tiny hairs at base. Shape: Ovate. Length: 0.8 cm. Width: 0.7 cm. Apex: Rounded to emarginate, cleaved. Margin: Entire. Color: Upper petal lobe (both upper and lower surfaces): Closest to RHS 9A (Yellow) with veins of RHS 187A (Greyed-Purple); veins have moderate to weak conspicuousness. Lower petal lobes: Upper surface is closest to RHS 5B (Yellow) with veins of RHS N187A (Greyed-Purple); lower surface is closest to RHS 8B (Yellow). Corolla tube: Length: 0.5 cm. Color, both inner and outer surfaces: RHS 9A (Yellow) with RHS 187A (Greyed-purple) veins.

*Sepal*.—Shape: Elliptical. Apex: Obtuse. Margin: Entire. Base: Truncate. Texture: Smooth and glabrous for both upper and lower surfaces. Color: RHS 144A (Yellow-Green) for both upper and lower surfaces. Length: 5.5 mm. Diameter: 2.5 mm. Average number of sepals per flower: 5.

*Peduncle*.—Length: 2.2 cm. Diameter: 0.5 mm. Color: RHS 144A (Yellow-Green). Texture: Smooth, glabrous. Strength: Moderately strong, wire-like.

Reproductive organs:

*Ovary color*.—RHS N144C (Yellow-Green).

*Pistil number*.—1 per inflorescence.

*Pistil length*.—3.0 mm.

*Stigma shape*.—Oval.

*Stigma color*.—RHS N144C (Yellow-Green).

*Style length*.—1.0 mm.

*Stamens number*.—4, free.

*Filament length*.—Greater than 1.0 mm.

*Filament color*.—RHS 144D (Yellow-Green).

*Anther shape*.—Oval, bi-lobed.
*Anther length*.—0.2 mm.
*Anther color*.—RHS 144A (Yellow-Green).
*Pollen amount*.—Abundant.
*Pollen color*.—RHS 155D (White).
*Seed production*.—Absent.

COMPARISON WITH PARENTAL LINES AND KNOWN VARIETY

'INTAMEC003' is distinguished from its parents as shown in Table 1 below:

TABLE 1

Comparison with Parental Lines

| Characteristic | 'INTAMEC003' | Female parent, wild line | Male parent 'AM5-264' |
|---|---|---|---|
| Flower color | Yellow | Yellow | Yellow |
| Plant growth habit | Compact | Upright | Compact/creeping |
| Leaf size | Large | Large | Small |

'INTAMEC003' is most similar to the commercial *Mecardonia* variety 'SAKMEC002' (U.S. Plant Pat. No. 24,515); however there are differences as described in Table 2 below.

TABLE 2

Comparison with Similar Variety

| Characteristic | 'INTAMEC003' | 'SAKMEC002' |
|---|---|---|
| Petal lobe color | Lower petal lobes, upper surface: Closest to RHS 5B (Yellow) with veins of RHS Ni 87A (Greyed-Purple) Upper petal lobe, upper surface: Closest to RHS 9A (Yellow) with veins of RHS 187A (Greyed-Purple) | Closest to RHS 9A (Yellow) with upper petal having veins of RHS N186A (Greyed-Purple) |
| Flower size (diameter) | 1.6 cm | 1.5 cm |
| Plant growth habit | Very Compact | Compact, freely branching |
| Earliness to flower | Extra-early | Extra-early |

I claim:

1. A new and distinct variety of *Mecardonia* plant as shown and described herein.

* * * * *